(12) United States Patent
Gilchrist et al.

(10) Patent No.: US 11,417,198 B1
(45) Date of Patent: Aug. 16, 2022

(54) PORTABLE DAMAGE CONTROL APPARATUS FOR MODULAR NETWORKS

(71) Applicant: United States of America as represented by the Secretary of the Navy, San Diego, CA (US)

(72) Inventors: Jeffery T. Gilchrist, San Diego, CA (US); William A. Chambers, San Diego, CA (US); Tyler J. Browe, San Diego, CA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 17/494,678

(22) Filed: Oct. 5, 2021

(51) Int. Cl.
| | |
|---|---|
| *G08C 17/02* | (2006.01) |
| *G08B 25/00* | (2006.01) |
| *B63B 79/10* | (2020.01) |
| *G01N 33/00* | (2006.01) |
| *G01K 1/024* | (2021.01) |
| *G08B 21/18* | (2006.01) |

(Continued)

(52) U.S. Cl.
CPC ............ *G08B 25/009* (2013.01); *B63B 79/10* (2020.01); *G01K 1/024* (2013.01); *G01K 3/005* (2013.01); *G01N 33/0063* (2013.01); *G08B 7/06* (2013.01); *G08B 21/18* (2013.01)

(58) Field of Classification Search
CPC ........ G08B 25/009; G08B 7/06; G08B 21/18; B63B 79/10; G01K 1/024; G01K 3/005; G01N 33/0063
See application file for complete search history.

(56) References Cited

U.S. PATENT DOCUMENTS

| | | |
|---|---|---|
| 8,717,163 B2 | 5/2014 | Easley et al. |
| 10,134,265 B2 | 11/2018 | Hess et al. |
| 10,950,118 B2 | 3/2021 | Brown et al. |

(Continued)

FOREIGN PATENT DOCUMENTS

| | | | | |
|---|---|---|---|---|
| AU | 2017201585 B2 | | 1/2019 | |
| KR | 20070107313 | * | 11/2007 | ............. G06Q 10/08 |
| KR | 20130034497 | * | 4/2013 | ........... G08B 21/187 |

*Primary Examiner* — Hongmin Fan
(74) *Attorney, Agent, or Firm* — Naval Information Warfare Center, Pacific; Kyle Eppele; Evan Hastings

(57) ABSTRACT

A modular damage control system and portable damage control apparatus for integrating damage control monitoring information with a transport vessel's centralized monitoring system. The modular damage control system includes a centralized monitoring system, portable equipment installation, at least one alarm, and a relay enclosure. The portable damage control apparatus includes at least one alarm and a relay enclosure, further comprising an external power supply, relay, end of line resistor, and alert device. The portable damage control apparatus allows for plug-and-play type integration with a centralized monitoring system, wherein the system described herein can enable the monitoring of hazards to a portable equipment installation by interfacing with a transport vessel's damage control network. The invention may also include a maritime vessel, intermodal containers, a potentiometer, discrete resistors, and an interface panel for displaying information specifying the alarm state to a crew member of the transport vessel.

20 Claims, 3 Drawing Sheets

(51) Int. Cl.
*G08B 7/06* (2006.01)
*G01K 3/00* (2006.01)

(56) References Cited

U.S. PATENT DOCUMENTS

2006/0255931 A1   11/2006   Hartsfield et al.
2013/0328697 A1*  12/2013   Lundy .................. G08B 25/009
                                                        340/870.01

* cited by examiner

PORTABLE DAMAGE CONTROL APPARATUS FOR MODULAR NETWORKS

FEDERALLY-SPONSORED RESEARCH AND DEVELOPMENT

The United States Government has ownership rights in this invention. Licensing inquiries may be directed to Office of Research and Technical Applications, Space and Naval Warfare Systems Center, Pacific, Code 72120, San Diego, Calif., 92152; telephone (619) 553-5118; email: ssc_pac_t2@navy.mil, referencing NC 111656.

FIELD OF THE INVENTION

The present disclosure pertains generally to modular damage control systems. More particularly, the present disclosure pertains to a portable damage control apparatus having modular integration with transport vessels.

BACKGROUND OF THE INVENTION

Transport vessels carry all manner of goods and portable installations around the world. These vessels utilize a number of onboard control systems to help with the monitoring and management of the vessel and its cargo. Advances in onboard control systems have reduced the number of crew members required to support a transport vessel, enabling smaller teams and reduced costs. Among the onboard control systems requiring significant support are damage control networks for identifying hazards. By centralizing the monitoring of damage control systems, crew members are freed up from manually monitoring these hazards. While some portable installations come readily equipped for integration with the transport vessel's damage control network, many do not. There is a need for a portable damage control apparatus for modular networks that readily integrates with the onboard centralized system to minimize the need for manual monitoring.

SUMMARY OF THE INVENTION

According to illustrative embodiments, a modular damage control system 10 for use on a transport vessel. Further, a portable damage control apparatus 20 for modular integration with a centralized monitoring system. Finally, a method of using a portable damage control apparatus.

BRIEF DESCRIPTION OF THE DRAWINGS

The accompanying drawings, which are incorporated in and form a part of the specification, illustrate example embodiments and, together with the description, serve to explain the principles of the invention. Throughout the several views, like elements are referenced using like references. The elements in the figures are not drawn to scale and some dimensions are exaggerated for clarity. In the drawings.

DETAILED DESCRIPTION OF THE EMBODIMENTS

Figure 1:
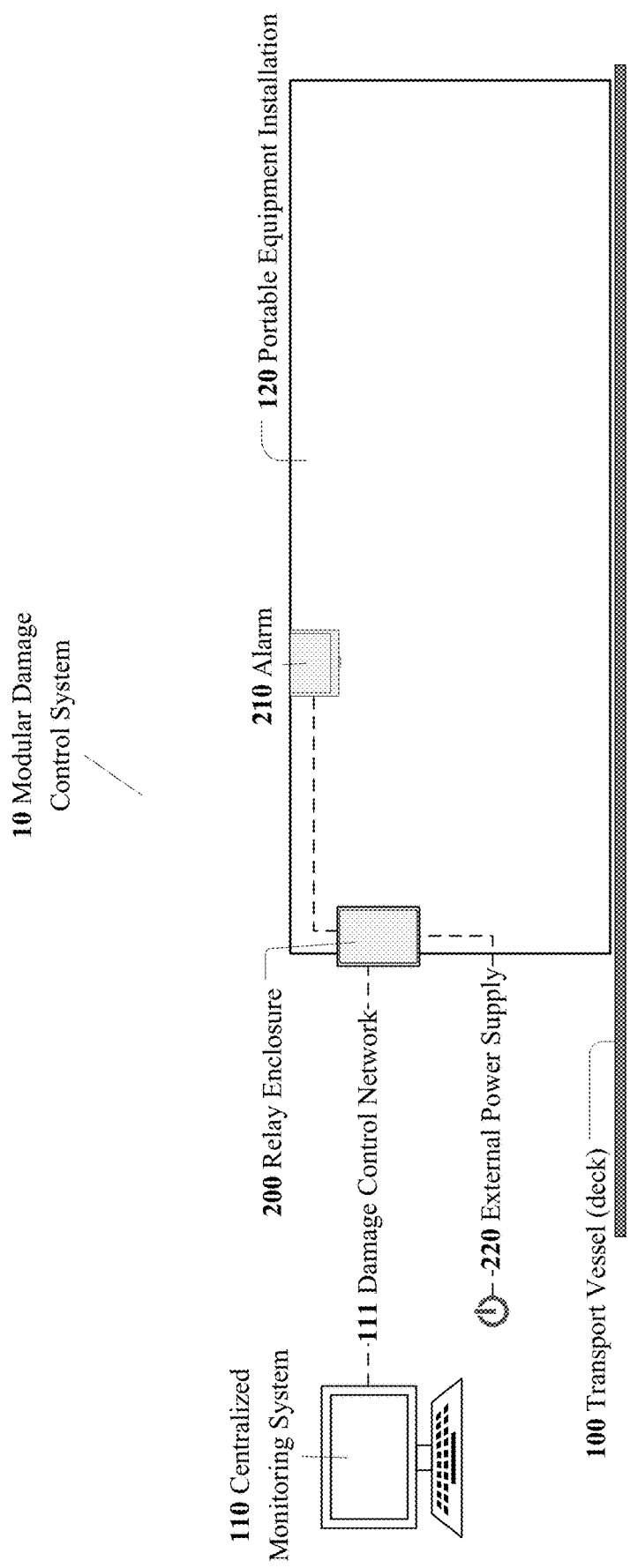
FIG. 1 is a block diagram of an example modular damage control system 10.

The portable damage control apparatus for modular networks below may be described generally, as well as in terms of specific examples and/or specific embodiments. For instances where references are made to detailed examples and/or embodiments, it should be appreciated that any of the underlying principles described are not to be limited to a single embodiment, but may be expanded for use with any of the other methods and systems described herein as will be understood by one of ordinary skill in the art unless otherwise stated specifically.

The portable damage control apparatus 20 for modular networks comprises a modular damage control system 10 and a portable damage control apparatus 20.

The modular damage control system 10 is a system of damage control monitoring that provides supplemental sensing/detection to a damage control network 111. Transport vessels 100 may have integrated damage control networks 111 that allow for hazard monitoring throughout the vessel. There is a need for expanding the damage control monitoring system when a transport vessel 100 facilitates non-integrated cargo. For example, an intermodal container without existing damage control monitoring could have such functionality supplemented and integrated with the centralized monitoring system 110. This supplementation and integration allows distinct portable equipment installations 120 their own damage control monitoring ability. In one embodiment, an intermodal container loaded onto the transport vessel could temporarily (during loading, transport, and unloading, etc. . . . ) have modular integration with transport vessel's 100 damage control system. This is desired to increase safety aboard the vessel and lessen the monitoring workload of the crew members.

The portable damage control apparatus 20 enables plug-and-play type interfacing between a portable damage control apparatus 20 and a transport vessel's 100 centralized monitoring system 110. In one embodiment, installation of the portable damage control apparatus 20 may include placing an alarm 210 in a well-situated position to detect hazards to the portable equipment installation 120, securing a relay enclosure 200 to the portable equipment installation 120, and connecting to the transport vessel's 100 external power supply 220 and damage control network 111. After the portable damage control apparatus 20 is installed, it can monitor for hazards to the portable equipment installation 102 and provide alarm state and system health information to the centralized monitoring 110. This facilitates the expansion of a transport vessel's 100 existing damage control network and provides distinct portable equipment installations 120 their own damage control monitoring functionality.

FIG. 1 is a block diagram of an embodiment of a modular damage control system 10 that can alert crew members aboard a transport vessel 100 to hazards threatening a portable equipment installation 120. The modular damage control system 10 may be used in any environment where the transport vessel is equipped with a damage control network and a centralized monitoring system 110. The modular damage control system 10 comprises, consists of, or consists essentially of a centralized monitoring system 110, a portable equipment installation 120, at least one alarm 210, and a relay enclosure 200.

While the centralized monitoring system 110 in FIG. 1 is shown as being connected via a damage control network 111 to the relay enclosure 200 via hardwiring, it is to be understood that data control network 111 is not so limited. In one embodiment, the centralized monitoring system 110 may be remote to the relay enclosure 200 and receiving information via, for example, Wi-Fi. The information being received by the centralized monitoring system 110 includes, but is not limited to, information pertaining to an alarm state and information pertaining to the system health and electrical continuity of the relay enclosure 200. The centralized monitoring system 110 then provides the aforementioned information to the crew of the transport vessel.

The portable equipment installation 120 can be loaded onto a transport vessel 100 and can interface with the centralized monitoring system 110. In the embodiment of the modular damage control system 10 shown in FIG. 1, the portable equipment installation 120 is rectangular. However, it is understood that the portable equipment installation 120 is not limited to rectangular geometries, but may be any shape loadable onto a transport vessel with an external power supply 220 and damage control network 111. In one embodiment, the portable equipment installation 120 may be an intermodal container. In another embodiment, the portable equipment installation 120 may be a trailer.

The alarm 210 is capable of detecting hazards to the portable equipment installation 120, which comprise, but are not limited to, a rapid rise in temperature, smoke, and carbon monoxide. The alarm 210 is comprised of a variety of hazard detection components, where each component is capable of detecting a unique hazard. The alarm is situated in a location or multiple locations that include but are not limited to, on top of, inside, and mounted to a side of the portable equipment installation 120. The location is such that a hazard to the portable equipment installation 120 would be detectable by the variety of hazard components. When a hazard component makes a detection, a change in alarm state is triggered within the alarm. The alarm state is comprised of information regarding whether a hazard has been detected and which hazard component has made the detection. Information regarding the alarm state is then transmitted to the relay within the relay enclosure 200. The alarm 210 may be used in any environment where the detection of hazards is desired. In one embodiment, it is desired for the alarm 210 has a ruggedized shell capable of withstanding the wear and tear of commercial transport.

The relay enclosure 200 comprises, consists of, or consists essentially of the relay 201, end of line resistor 202, and alert device 203. The relay enclosure 200 has an internal cavity 204 and defined by an outer shell 205. The relay enclosure 200 is for receiving alarm state information from an alarm, transmitting alarm state information to a centralized monitoring system 110, and providing electrical continuity status to the centralized monitoring system 110. The relay enclosure 200 may receive power from a suitable external power supply 220. The relay enclosure 200 is made of any desired material suitable for a commercial transport environment. In one embodiment, the relay enclosure 200 is ruggedized for use in military applications. The relay enclosure 200 is coupled to the portable equipment installation 120 in a way that allows for the monitoring of hazards to the portable equipment installation 120.

The transport vessel 100 is of a type that has an integrated damage control network 111 for centralized monitoring. The transport vessel 100 operates modularly with its cargo to allow for interfacing between the cargo and the vessel. One having ordinary skill in the art would appreciate that the interfacing elements may include, but are not limited to an external power supply 220 and a damage control network. In the embodiment of the transport vessel 100 in FIG. 1, the transport vessel 100 has a deck. However, it is to be understood that the transport vessel 100 is not limited vessels having decks. In one embodiment, the transport vessel 100 may be a maritime vessel. In another embodiment, the transport vessel 100 may be a cargo ship having an interface with an intermodal container where the interface comprises, consists of, or consists essentially of, a damage control network 111 and an external power supply 220.

The external power supply 220 may be any power source capable of providing power to the relay enclosure 200. In one embodiment, the external power supply 220 is a component of interface between the portable equipment installation 120 and the transport vessel 100. In one embodiment, a suitable power source would be 115 VAC 60 Hz single-phase continuous power. In another embodiment example, a suitable power source would be a battery.

The damage control network 111 facilitates transmission of damage control information between the portable equipment installation 120 and the centralized monitoring system 110. While the damage control network 111 in FIG. 1 is shown as hardwiring, it is to be understood that data control network 111 is not so limited. In one embodiment, the damage control network 111 transmits data via hardwiring. In another embodiment, the damage control network 111 transmits data via wireless protocols.

Figure 2:
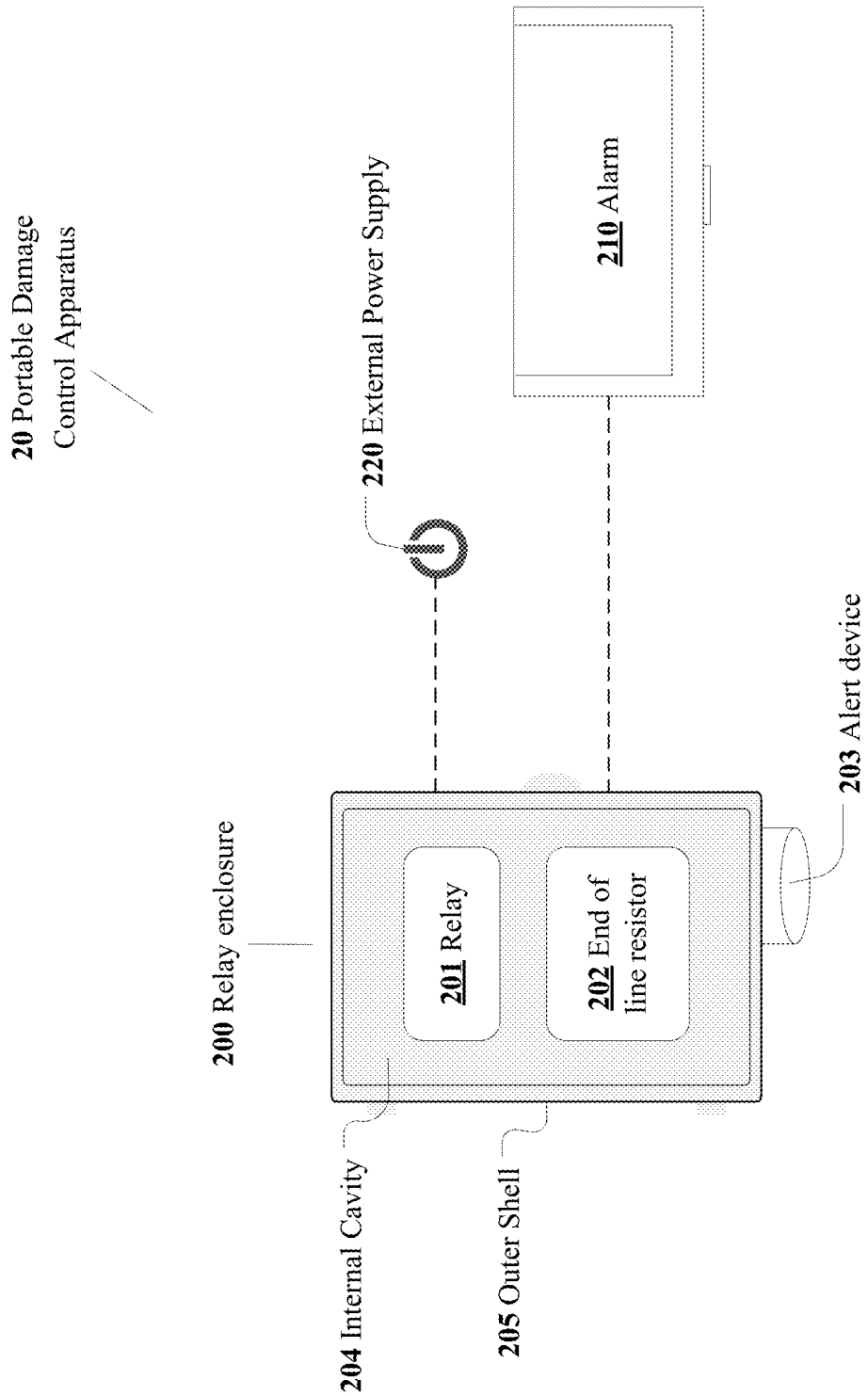
FIG. 2 is a block diagram of an example portable damage control apparatus 20 for modular integration with a centralized monitoring system.

FIG. 2 is a block diagram of a portable damage control apparatus 20 for modular integration with a centralized monitoring system 110. The portable damage control apparatus 20 allows for plug-and-play type integration with a centralized monitoring system 110, wherein the portable damage control apparatus 20 described herein can enable the monitoring of hazards to a portable equipment installation 120 by interfacing with a transport vessel's 100 damage control network 111. It is understood that some portable equipment installations 102 have existing integrated damage control systems. In one embodiment, the portable damage control apparatus 20 for modular integration provides supplemental damage control monitoring to a portable equipment installation 120. In another embodiment, the portable damage control apparatus 20 provides damage control monitoring to a portable equipment installation 120 not having an existing damage control system.

The relay 201 is positioned inside the relay enclosure 200. The relay 201 receives alarm state information from at least one alarm 210, and transmits alarm state information to a centralized monitoring system 110. The relay 201 provides continuous information regarding the alarm state to the centralized monitoring system 110. In one embodiment, the relay 201 is an electrically operated switch, wherein the relay 201 consists of input terminals for single or multiple signals. In another embodiment, the relay 201 can facilitate receiving alarm state information and transmitting alarm state information to the centralized monitoring system 110 for up to four alarms 210.

The end of line resistor 202 provides an indication of electrical continuity to the centralized monitoring system 110. The centralized monitoring system 110 continuously monitors the status resistance of the end of line resistor 202 to confirm system health. Poor system health is indicated by a change in status resistance, and may be attributed to damaged or disconnected wiring of the portable damage control apparatus 20.

The centralized monitoring system 110 receives continuous information from the end of line resistor 202 regarding electrical continuity and the associated alarm state. Continuous monitoring is desired so that the crew may immediately respond to a change in alarm state or indication of faulty connectivity.

In one embodiment, the end of line resistor 202 comprises, consists of, or consists essentially of a resistor of a known resistance which may be, for example, 470Ω or 6800Ω.

In another embodiment, the end of line resistor 202 comprises, consists of, or consists essentially of a potentiometer capable of providing a variable resistance. A potentiometer having a variable resistance enables compatibility between the portable damage control apparatus 20 and transport vessels 100 with unique system requirements. It is understood that transport vessels 100 may have unique requirements for their damage control network 111 and centralized monitoring system 110. Wherein the end of line resistor 202 comprises a potentiometer, the potentiometer is selectively set to a resistance compatible with a transport vessel's 100 centralized monitoring system 110. The potentiometer, preferably, can select within a range of resistances between 1 and 10 kΩ However, it is understood that the potentiometer may not include all aforementioned resistances. The selected resistance may include 470Ω or 6800Ω, for instance. The potentiometer may be used where it is desired to have a plurality of known resistances for modular integration with unique central monitoring systems 110.

The alert device 203 produces a localized alert when triggered by a change in an alarm state. In one embodiment the alert signal is an audible warning signal. For example, when a fire is detected by the alarm, the alert device may sound a siren. In another embodiment, the alert signal may emit light. In another embodiment, the alert signal may produce a tactical vibration. The alert device 203 is coupled to the outer shell 205 of the relay enclosure 200. The size and shape of the alert device is driven by the desired performance characteristics, which may include, for example, volume, as well as the constraints of the size of the relay enclosure 200, to which it is mounted.

Figure 3:
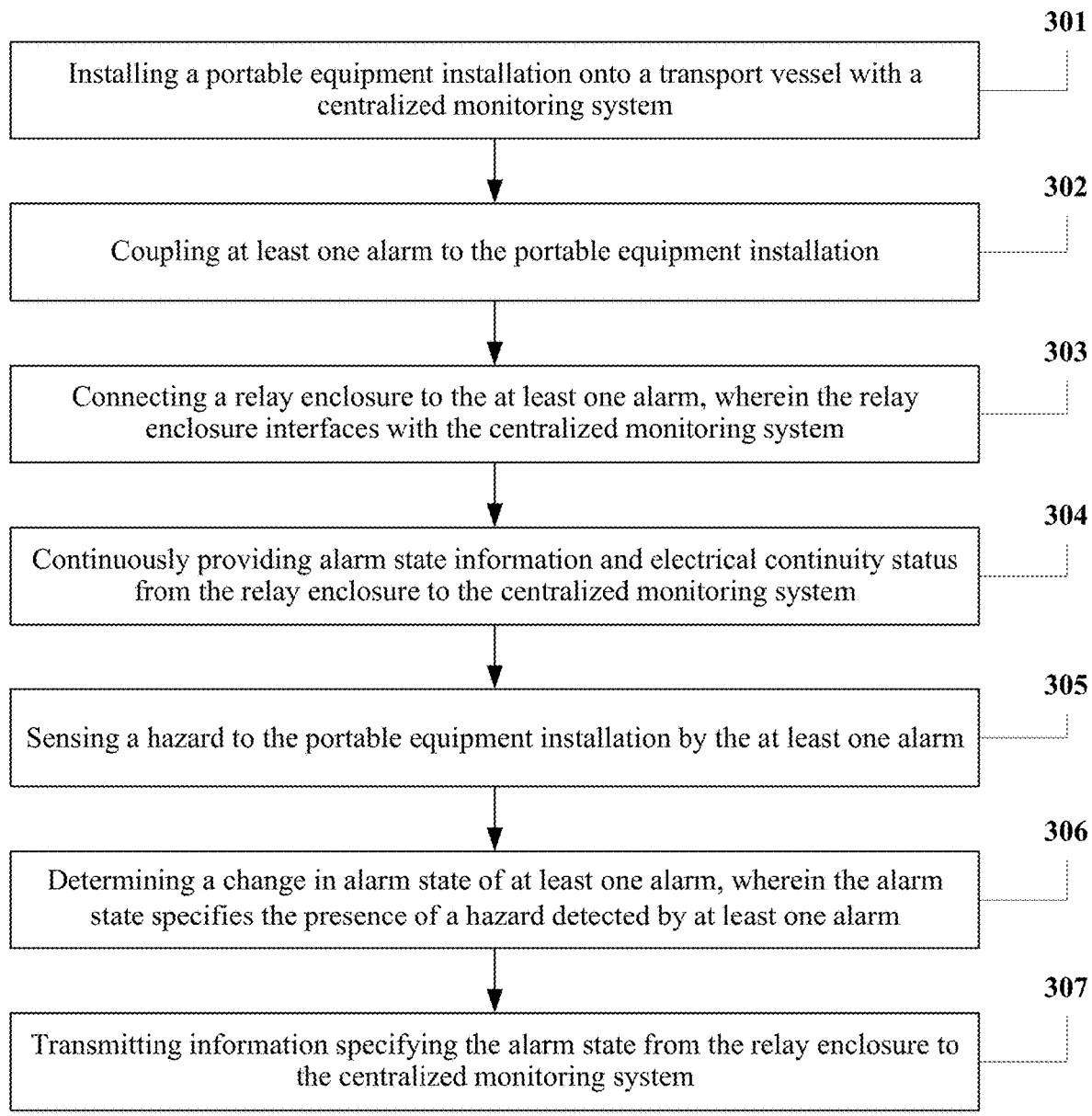
FIG. 3 is a flowchart illustrating operations of a method of using a portable damage control apparatus.

FIG. 3 is a flowchart illustrating operations of a method of using a portable damage control apparatus. One step 301 provides for installing a portable equipment installation 120 onto a transport vessel 100 with a centralized monitoring system 110. Another step 302 provides for coupling at least one alarm 210 to the portable equipment installation 120. Another step 303 provides for connecting a relay enclosure 200 to the at least one alarm 210, wherein the relay enclosure 200 interfaces with the centralized monitoring system 110. Another step 304 provides for continuously providing alarm state information and electrical continuity status from the relay enclosure 200 to the centralized monitoring system 110. Another step 305 provides for sensing a hazard to the portable equipment installation 120 by the at least one alarm 210. Another step 306 provides for determining a change in alarm state of at least one alarm 210, wherein the alarm state specifies the presence of a hazard detected by at least one alarm 210. Another step 307 provides for transmitting information specifying the alarm state from the relay enclosure 200 to the centralized monitoring system 110.

In one embodiment, the method of using a portable damage control apparatus may include displaying information to transport vessel personnel specifying the alarm state on a vessel interface display. In another embodiment, the method of using a portable damage control apparatus may include displaying information to transport vessel personnel regarding the electrical continuity status on a vessel interface display.

In another embodiment, method of using a portable damage control apparatus may include hazard detection for a rapid temperature rise, carbon monoxide, and airborne smoke.

What is claimed is:
1. A modular damage control system, comprising:
 a centralized monitoring system for receiving information from a damage control network;
 a portable equipment installation for modular integration with aft transport vessel, wherein the portable equipment installation interfaces with the transport vessel, the interfacing comprising: an external power supply and the damage control network;
 at least one alarm for detecting a hazard to the portable equipment installation, each of the at least one alarm having an alarm state specifying the hazard; and
 a relay enclosure configured to receive alarm state information from the at least one alarm, the relay enclosure further configured to transmit the alarm state information to the centralized monitoring system via the damage control network, wherein the relay enclosure provides end of line continuity to the centralized control monitoring system.

2. The modular damage control system of claim 1, wherein the relay enclosure comprises an end of line resistor having a known discrete value for providing electrical continuity.

3. The modular damage control system of claim 1, wherein the relay enclosure comprises a potentiometer for selectively tuning to a discrete resistance value compatible with the centralized monitoring system.

4. The modular damage control system of claim 1, wherein the centralized monitoring system has an interface panel for displaying information specifying the alarm state to a crew member of the transport vessel.

5. The modular damage control system of claim 1, wherein the portable equipment installation is an intermodal container, wherein the intermodal container can be used across a plurality of transport vessels.

6. The modular damage control system of claim 1, where in the transport vessel is a maritime vessel.

7. The modular damage control system of claim 1, wherein centralized monitoring system is located on board the transport vessel.

8. A portable damage control apparatus for modular integration with a centralized monitoring system, comprising:
 at least one alarm for detecting the presence of a hazard, the at least one alarm coupled to a portable equipment installation, each of the at least one alarm having an alarm state specifying the hazard;
 a relay enclosure connected to the at least one alarm, comprising:
  an external power supply;
  a relay for receiving information specifying the alarm state from the at least one alarm, the relay further for transmitting information specifying the alarm state of the at least one alarm to the centralized monitoring system;
  an end of line resistor for providing electrical continuity status to the centralized monitoring system; and
  an alert device responsive to the alarm state of the at least one alarm, the alert device for producing a localized alert signal.

9. The portable damage control apparatus of claim 8, wherein the end of line resistor is a potentiometer for selectively tuning to a discrete resistance value compatible with the centralized monitoring system.

10. The portable damage control apparatus of claim 8, wherein the end of line resistor has a discrete resistance value.

11. The portable damage control apparatus of claim 10, wherein the end of line resistor has a discrete resistance value of 470 Ω.

12. The portable damage control apparatus of claim 10, wherein the end of line resistor has a discrete resistance value of 6800 Ω.

13. The portable damage control apparatus of claim 8, wherein the external power supply is a battery.

14. The portable damage control apparatus of claim 8, wherein the external power supply is adapted for 115 VAC 60 Hz single-phase power.

15. The portable damage control apparatus of claim 8, wherein the alert signal is an audible warning signal.

16. The portable damage control apparatus of claim 8, wherein the alarm state indicates the hazard is a type selected from a group consisting of rapid temperature rise, carbon monoxide, and airborne smoke.

17. A method of using a portable damage control apparatus, comprising:
  installing a portable equipment installation onto a transport vessel with a centralized monitoring system;
  coupling at least one alarm to the portable equipment installation;
  connecting a relay enclosure to the at least one alarm, wherein the relay enclosure interfaces with the centralized monitoring system;
  continuously providing alarm state information and electrical continuity status from the relay enclosure to the centralized monitoring system;
  sensing a hazard to the portable equipment installation by the at least one alarm;
  determining a change in alarm state of at least one alarm, wherein the alarm state specifies the presence of a hazard detected by at least one alarm; and
  transmitting information specifying the alarm state from the relay enclosure to the centralized monitoring system.

18. The method of using a portable damage control apparatus of claim 17, further comprising:
  displaying information to transport vessel personnel by specifying the alarm state on a vessel interface display.

19. The method of using a portable damage control apparatus of claim 17, further comprising:
  displaying information to transport vessel personnel regarding the electrical continuity on a vessel interface display.

20. The method of using a portable damage control apparatus of claim 17, wherein the hazard detected is a type selected from a group consisting of rapid temperature rise, carbon monoxide, and airborne smoke.

\* \* \* \* \*